US010490837B2

(12) United States Patent
Kono et al.

(10) Patent No.: US 10,490,837 B2
(45) Date of Patent: Nov. 26, 2019

(54) BIOREACTOR COMPRISING IMMOBILIZED ENZYME, METHOD FOR IMPROVING ACTIVITY OF IMMOBILIZED ENZYME, AND BIOFUEL CELL (71) Applicant: TOYOTA JIDOSHA KABUSHIKI KAISHA, Toyota-shi, Aichi (JP)

(72) Inventors: Noriko Kono, Tajimi (JP); Takahiro Kusumegi, Toyota (JP); Yusaku Onochi, Toyota (JP); Tatsuhiro Sugimoto, Toyota (JP)

(73) Assignee: TOYOTA JIDOSHA KABUSHIKI KAISHA, Toyota-shi, Aichi-ken (JP)

(*) Notice: Subject to any disclaimer, the term of this patent is extended or adjusted under 35 U.S.C. 154(b) by 0 days.

(21) Appl. No.: 14/650,365

(22) PCT Filed: Dec. 18, 2013

(86) PCT No.: PCT/JP2013/083959
§ 371 (c)(1),
(2) Date: Jun. 8, 2015

(87) PCT Pub. No.: WO2014/098153
PCT Pub. Date: Jun. 26, 2014

(65) Prior Publication Data
US 2015/0315549 A1 Nov. 5, 2015

(30) Foreign Application Priority Data

Dec. 19, 2012 (JP) .................................. 2012-277271

(51) Int. Cl.
*H01M 8/16* (2006.01)
*C12N 9/02* (2006.01)
*C12N 11/00* (2006.01)
*C12N 11/02* (2006.01)
*C12M 1/40* (2006.01)
*C12N 9/04* (2006.01)
*C12N 9/06* (2006.01)

(52) U.S. Cl.
CPC .............. *H01M 8/16* (2013.01); *C12M 21/18* (2013.01); *C12N 9/0004* (2013.01); *C12N 9/0006* (2013.01); *C12N 9/0008* (2013.01); *C12N 9/0016* (2013.01); *C12N 11/00* (2013.01); *C12N 11/02* (2013.01); *C12Y 101/01* (2013.01); *C12Y 102/01* (2013.01); *C12Y 104/01* (2013.01); *Y02E 60/527* (2013.01)

(58) Field of Classification Search
CPC .... C12N 9/0004; C12N 9/0008; C12N 11/00; C12N 9/008; C12N 9/0006; C12N 11/02; C12M 21/18; H01M 8/16; H01M 8/22; H01M 8/222; Y02E 60/527
See application file for complete search history.

(56) References Cited

U.S. PATENT DOCUMENTS

| 5,858,695 A | 1/1999 | Kadota et al. |
| 6,773,564 B1 | 8/2004 | Yugawa et al. |
| 6,773,654 B2 | 8/2004 | Yugawa et al. |
| 7,955,741 B2 | 6/2011 | Sakai et al. |
| 8,440,333 B2 | 5/2013 | Nakagawa et al. |
| 9,074,239 B2 | 7/2015 | Tajima et al. |
| 2005/0049313 A1* | 3/2005 | Nishizawa ............ C07C 235/78 514/682 |
| 2005/0191735 A1* | 9/2005 | Bobkova .................. C12P 7/62 435/135 |
| 2007/0131546 A1 | 6/2007 | Nomoto et al. |
| 2007/0224466 A1 | 9/2007 | Nakagawa et al. |
| 2009/0053582 A1 | 2/2009 | Sugiyama et al. |
| 2009/0117638 A1 | 5/2009 | Kumita et al. |
| 2010/0040910 A1* | 2/2010 | Kajino ................. C12N 9/0091 429/401 |
| 2010/0178572 A1 | 7/2010 | Kato et al. |
| 2010/0221644 A1* | 9/2010 | Nakagawa .......... H01M 4/9008 429/523 |
| 2010/0310946 A1* | 12/2010 | Sakai ...................... H01M 4/86 429/408 |
| 2011/0053005 A1* | 3/2011 | Heller ..................... H01M 8/16 429/401 |
| 2011/0076736 A1 | 3/2011 | Matsumoto et al. |
| 2011/0200889 A1 | 8/2011 | Kumita et al. |

(Continued)

FOREIGN PATENT DOCUMENTS

| CN | 101682070 A | 3/2010 |
| CN | 101908630 A | 12/2010 |
| JP | 09-178755 A | 7/1997 |
| JP | 10-75779 A | 3/1998 |
| JP | 2000-171428 A | 6/2000 |
| JP | 2001-120263 A | 5/2001 |

(Continued)

OTHER PUBLICATIONS

"Polymer." in: Britannica Academic, Encyclopaedia Britannica. Oct. 19, 2017. [online]. [retrieved on Sep. 6, 2018]. Retrieved from the Internet:<URL: http://academic.eb.com/levels/collegiate/article/polymer/60700. (Year: 2017).*

(Continued)

*Primary Examiner* — Renee Claytor
*Assistant Examiner* — Susan E. Fernandez
(74) *Attorney, Agent, or Firm* — Sughrue Mion, PLLC (57) ABSTRACT According to the present invention, the enzyme activity of an immobilized enzyme is improved regardless of enzyme type. A bioreactor, comprising an immobilized enzyme and a heterocyclic compound containing nitrogen and carbon atoms and having 5- or 6-membered ring, which form a reaction field, wherein the immobilized enzyme is allowed to cause an enzymatic reaction in the reaction field is, provided.

8 Claims, 5 Drawing Sheets (56) References Cited

U.S. PATENT DOCUMENTS

| | | |
|---|---|---|
| 2011/0229776 A1 | 9/2011 | Kumita et al. |
| 2013/0161204 A1 | 6/2013 | Uchiyama et al. |
| 2014/0272608 A1 | 9/2014 | Kusumegi et al. |

FOREIGN PATENT DOCUMENTS

| | | |
|---|---|---|
| JP | 2005-310613 A | 11/2005 |
| JP | 2006-24555 A | 1/2006 |
| JP | 2006-49215 A | 2/2006 |
| JP | 2006-93090 A | 4/2006 |
| JP | 2006-208299 A | 8/2006 |
| JP | 2007-163185 A | 6/2007 |
| JP | 2008-060067 A | 3/2008 |
| JP | 2008-071584 A | 3/2008 |
| JP | 2008-161178 A | 7/2008 |
| JP | 2009-044997 A | 3/2009 |
| JP | 2009-158458 A | 7/2009 |
| JP | 2009-158480 A | 7/2009 |
| JP | 2009-247289 A | 10/2009 |
| JP | 2010-183857 A | 8/2010 |
| WO | 2010/041685 A1 | 4/2010 |
| WO | 2010/129940 A2 | 11/2010 |
| WO | 2012/042903 A1 | 4/2012 |
| WO | 2012/169512 A1 | 12/2012 |

OTHER PUBLICATIONS

Kenji Ishibashi et al., "Pentacyanoferrate and Bilirubin Oxidase-bound Polymer for Oxygen Reduction Bio-cathode", Electrochemistry, 2008, pp. 594-596, vol. 76, No. 8.
International Search Report of PCT/JP2013/083959 dated Mar. 18, 2014 [PCT/ISA/210].
Partial English Translation of Chinese Office Action dated Jul. 28, 2016 in counterpart Chinese Application No. 201380066363.9.
Office Action from the U.S. Patent and Trademark Office dated Aug. 5, 2016, for U.S. Appl. No. 14/349,777.
Seiya Tsujimura et al., "Recent Development of Enzyme-based Biofuel Cells", GS Yuasa Technical Report, 2008, vol. 5, No. 2, pp. 1-6 (7 pages total).
Gerd J. Mander et al., "Use of Laccase as a Novel, Versatile Reporter System in Filamentous Fungi", Applied and Environmental Microbiology, vol. 72, No. 7, XP-002568245, Jul. 2006 (pp. 5020-5026).
T. Beneyton et al., "Immobilization of CotA, an Extremophilic Laccase from *Bacillus subtilis*, on Glassy Carbon Electrodes for Biofuel Cell Applications", Electrochemistry Communications, vol. 13, 2011 (pp. 24-27).

\* cited by examiner

BIOREACTOR COMPRISING IMMOBILIZED ENZYME, METHOD FOR IMPROVING ACTIVITY OF IMMOBILIZED ENZYME, AND BIOFUEL CELL

CROSS REFERENCE TO RELATED APPLICATIONS

This application is a National Stage of International Application No. PCT/JP2013/083959, filed Dec. 18, 2013, claiming priority based on Japanese Patent Application No. 2012-277271, filed Dec. 19, 2012, the contents of all which are incorporated herein by reference in their entirety.

TECHNICAL FIELD

The present invention relates to a bioreactor using an enzymatic reaction caused by an immobilized enzyme and a method for improving activity of an immobilized enzyme. Also, the present invention relates to a biofuel cell using an enzymatic reaction caused by an immobilized enzyme.

BACKGROUND ART

The term "bioreactor" refers to an apparatus using a biological reaction caused by an enzyme or the like. Immobilized enzymes, immobilized microorganisms, other viable cells, and the like are used in biological reactions for bioreactors. Bioreactors are used for production of amino acids, peptides, organic acids, and other substances, isomerization of sugars, and the like. In addition, bioreactors comprising enzymatic catalysts are used in some processes in the petrochemical industry. Further, some other bioreactors are used for analysis for a variety of diagnostics and the like.

Biofuel cells are also referred to as enzymatic fuel cells in which electric energy is generated through chemical reactions caused by enzymes and microorganisms. Biofuel cells have a structure in which a cathode electrode and an anode electrode face each other across an electrolyte, as do general battery cells. Fuels used in biofuel cells are alcohols such as methanol and ethanol or sugars such as glucose. In addition, an immobilized enzyme is used in the cathode electrode and the anode electrode of an electrode biofuel cell.

Both bioreactors and biofuel cells are expected to result in significantly improved substance productivity and electric output if reaction efficiency of the chemical reaction caused by an enzyme or the like can be improved. However, research on technology that can improve enzymatic reactions caused by immobilized enzymes in bioreactors and biofuel cells has not been successful. Therefore, technology that can be universally applied to bioreactors and biofuel cells comprising immobilized enzymes in order to significantly improve the efficiency of enzymatic reactions caused by the immobilized enzymes has been awaited.

Non-Patent Document 1 and Patent Document 1 disclose biofuel cells in which an electron transfer mediator is immobilized on an electrode. Polyvinylimidazole is used as a solidifying agent for immobilizing an electron transfer mediator on an electrode material for the biofuel cells disclosed in Non-Patent Document 1 and Patent Document 1. In addition, in the cases of biofuel cells disclosed in Non-Patent Document 1 and Patent Document 1, enzymes are dispersed in an electrolyte solution.

In addition, Patent Document 2 discloses a fuel cell having a structure in which a positive electrode and a negative electrode face each other across an electrolyte containing a buffer substance, an immobilized enzyme is used for either one or both of the positive electrode and the negative electrode, and a compound containing an imidazole ring is used as the buffer substance. The fuel cell disclosed in Patent Document 2 is produced by immobilizing bilirubin oxidase on a positive electrode and, when an electrolyte containing an imidazole buffer solution is used, a high current density is achieved for unipolar evaluation of a cathode electrode.

Further, Patent Document 3 discloses a sensor for measuring a blood sugar level using an enzyme and an electron receptor. The sensor disclosed in Patent Document 3 includes a heterocyclic compound such as imidazole as well as an enzyme and an electron receptor so as to improve preservation stability of the enzyme (for suppression of changes in the current value before, during, and after preservation).

PRIOR ART DOCUMENTS

Patent Documents

Patent Document 1: JP Patent Publication (Kokai) 2008-71584 A
Patent Document 2: JP Patent Publication (Kokai) 2008-60067 A
Patent Document 3: WO2012/042903

Non-Patent Documents

Non-Patent Document 1: Electrochemistry 76, No. 8, (2008) pp. 594-596

SUMMARY OF THE INVENTION

Problem to be Solved by the Invention

Meanwhile, there has been no well-known technology that can improve the enzyme activity of an immobilized enzyme in a bioreactor or a biofuel cell for a wide range of enzymes regardless of enzyme type. In view of the above circumstances, an object of the present invention is to provide: a bioreactor comprising an immobilized enzyme of an arbitrary type, which has excellent enzyme activity; a method for improving activity of an immobilized enzyme, whereby the enzyme activity of the immobilized enzyme can be improved regardless of enzyme type; and a biofuel cell comprising an immobilized enzyme having excellent enzyme activity.

Means for Solving the Problem

As a result of intensive studies conducted by the present inventors in order to achieve the above object, the present inventors found that when a heterocyclic compound containing nitrogen and carbon atoms and having 5- or 6-membered ring is present in a system of a reaction that is caused by an immobilized enzyme, the enzyme activity of the immobilized enzyme can be significantly improved. This has led to the completion of the present invention. The present invention encompasses the following (1) to (24).

(1) A bioreactor, comprising an immobilized enzyme and a reaction field including a heterocyclic compound containing a 5- or 6-membered ring of nitrogen and carbon atoms, wherein the immobilized enzyme is allowed to cause an enzymatic reaction in the reaction field.

(2) The bioreactor according to (1), wherein the concentration of the compound in the reaction field is 0.2-5.0 M.
(3) The bioreactor according to (1), wherein the immobilized enzyme is obtained by immobilizing an oxidoreductase on a support.
(4) The bioreactor according to (3), wherein the oxidoreductase is an enzyme that catalyzes a redox reaction with the use of NAD and/or NADP as an electron acceptor.
(5) The bioreactor according to (3), wherein the oxidoreductase is at least one enzyme selected from the group consisting of glucose-1-dehydrogenase, glutamate dehydrogenase, and formate dehydrogenase.
(6) The bioreactor according to (1), wherein the heterocyclic compound is a compound containing an imidazole ring.
(7) The bioreactor according to (1), wherein the heterocyclic compound is at least one compound selected from the group consisting of imidazole hydrochloride, pyrazine, 2-imidazolidinone, 1-vinylimidazole, polyvinyl imidazole, and histidine.
(8) A method for improving the enzyme activity of an immobilized enzyme, comprising allowing the immobilized enzyme to cause an enzymatic reaction in the presence of a heterocyclic compound containing nitrogen and carbon atoms and having 5- or 6-membered ring.
(9) The method for improving the enzyme activity of an immobilized enzyme according to (8), wherein the concentration of the compound is adjusted to 0.2-5.0 M in order to realize the enzymatic reaction.
(10) The method for improving the enzyme activity of an immobilized enzyme according to (8), wherein the immobilized enzyme is obtained by immobilizing an oxidoreductase on a support.
(11) The method for improving the enzyme activity of an immobilized enzyme according to (10), wherein the oxidoreductase is an enzyme that catalyzes a redox reaction with the use of NAD and/or NADP as an electron acceptor.
(12) The method for improving the enzyme activity of an immobilized enzyme according to (11), wherein the oxidoreductase is at least one enzyme selected from the group consisting of glucose-1-dehydrogenase, glutamate dehydrogenase, and formate dehydrogenase.
(13) The method for improving the enzyme activity of an immobilized enzyme according to (8), wherein the heterocyclic compound is a compound containing an imidazole ring.
(14) The method for improving the enzyme activity of an immobilized enzyme according to (8), wherein the heterocyclic compound is at least one compound selected from the group consisting of imidazole hydrochloride, pyrazine, 2-imidazolidinone, 1-vinylimidazole, polyvinyl imidazole, and histidine.
(15) A biofuel cell, comprising a cathode electrode and an anode electrode that face each other across an electrolyte, wherein the cathode electrode, the anode electrode, or both thereof comprise an immobilized enzyme, and the immobilized enzyme is allowed to cause an enzymatic reaction in the presence of a heterocyclic compound containing nitrogen and carbon atoms and having 5- or 6-membered ring.
(16) The biofuel cell according to (15), wherein the compound is contained in a fuel that comes into contact with the anode electrode and/or a solution that comes into contact with the cathode electrode.
(17) The biofuel cell according to (15), wherein the compound is present on the surface of the anode electrode with which a fuel comes into contact and/or the surface of the cathode electrode with which a solution comes into contact.
(18) The biofuel cell according to (15), wherein the concentration of the compound is adjusted to 0.2-5.0 M in order to realize the enzymatic reaction.
(19) The biofuel cell according to (15), wherein the immobilized enzyme is obtained by immobilizing an oxidoreductase on a support.
(20) The biofuel cell according to (19), wherein the oxidoreductase is an enzyme that catalyzes a redox reaction with the use of NAD and/or NADP as an electron acceptor.
(21) The biofuel cell according to (19), wherein the oxidoreductase is at least one enzyme selected from the group consisting of glucose-1-dehydrogenase, glutamate dehydrogenase, and formate dehydrogenase.
(22) The biofuel cell according to (15), wherein the anode electrode has an immobilized enzyme, and an enzymatic reaction takes place in the anode electrode in the presence of a heterocyclic compound containing nitrogen and carbon atoms and having 5- or 6-membered ring.
(23) The biofuel cell according to (15), wherein the heterocyclic compound is a compound containing an imidazole ring.
(24) The biofuel cell according to (15), wherein the heterocyclic compound is at least one compound selected from the group consisting of imidazole hydrochloride, pyrazine, 2-imidazolidinone, 1-vinylimidazole, polyvinyl imidazole, and histidine.

This description includes all or part of the contents as disclosed in the description and/or drawings of Japanese Patent Application No. 2012-277271, to which the present application claims priority.

EFFECTS OF THE INVENTION

According to the present invention, enzyme activity of an immobilized enzyme used in a bioreactor, a biofuel cell, or the like can be significantly improved regardless of enzyme type. The bioreactor of the present invention achieves excellent reaction efficiency in a reaction field because of the improved enzyme activity of an immobilized enzyme. The biofuel cell of the present invention has excellent fuel cell characteristics because of the improved enzyme activity of an immobilized enzyme.

EMBODIMENTS FOR CARRYING OUT THE INVENTION

The present invention is described in detail below with reference to the drawings.

When an immobilized enzyme obtained by immobilizing an enzyme on a support is used, the present invention is applicable, regardless of enzyme type. The enzyme activity of an immobilized enzyme can be improved with the present invention. Specifically, the effects of improving the enzyme activity obtained by the present invention are not limited to specific types of enzymes and thus can be achieved for a wide range of enzymes. In other words, the method for improving activity of an immobilized enzyme of the present invention is a technique whereby the enzyme activity of an immobilized enzyme prepared with an arbitrary enzyme can be improved. The method for improving activity of an immobilized enzyme of the present invention is characterized in that an immobilized enzyme is allowed to cause an enzymatic reaction in the presence of a heterocyclic compound containing nitrogen and carbon atoms and having 5- or 6-membered ring.

The method for improving activity of an immobilized enzyme of the present invention is applicable to any system using an immobilized enzyme. Specifically, examples of a system using an immobilized enzyme are bioreactors and biofuel cells. However, the method for improving activity of an immobilized enzyme of the present invention is not limited to such examples. The bioreactor and the biofuel cell of the present invention are described below.

<Bioreactor>

The bioreactor of the present invention is an apparatus comprising an immobilized enzyme and a reaction field including a heterocyclic compound containing nitrogen and carbon atoms and having 5- or 6-membered ring. In the bioreactor, the immobilized enzyme causes an enzymatic reaction to proceed in the reaction field; that is to say, the immobilized enzyme causes an enzymatic reaction in the presence of a heterocyclic compound containing nitrogen and carbon atoms and having 5- or 6-membered ring. In addition, the bioreactor of the present invention may be any of the following as long as it is an apparatus using a biological reaction caused by an immobilized enzyme: an apparatus for producing a substance, an apparatus for sensing a substance or the like, an apparatus for quantitative analysis of a substance or the like, an apparatus for detecting a change in a substance, and the like. That is, the scope of the bioreactor of the present invention includes biosensors.

In addition, the intended use of the bioreactor of the present invention is not particularly limited. Examples of the intended use include production of a variety of substances, detection of a variety of substances, and analysis for a variety of diagnostics.

Figure 1:
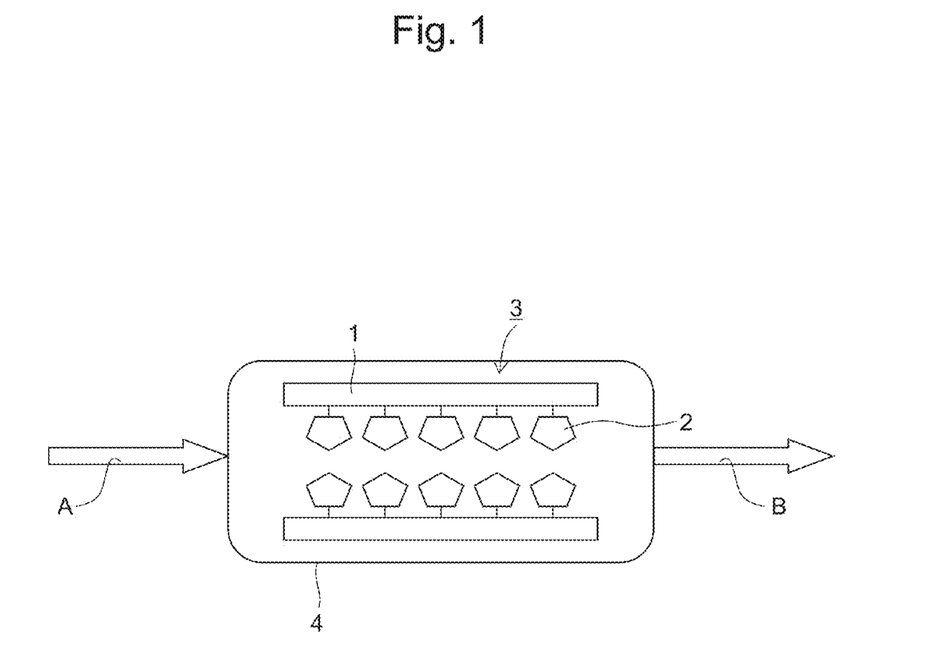
FIG. 1 schematically shows an example of the bioreactor of the present invention.

FIG. 1 schematically shows an example of the bioreactor of the present invention. The bioreactor shown in FIG. 1 is configured to have an immobilized enzyme 3 obtained by immobilizing an enzyme 2 on a support 1 and a chassis 4 accommodating the immobilized enzyme 3. An enzymatic reaction takes place in the chassis 4 so as to produce a substance of interest through the enzymatic reaction in the bioreactor shown in FIG. 1.

Specifically, when a reaction solution containing a substrate for a substance of interest is supplied to the chassis 4 as shown by arrow A in FIG. 1, an enzymatic reaction caused by the immobilized enzyme 3 proceeds in the chassis 4. That is, when the reaction solution is supplied to the chassis 4, a reaction field is formed in the chassis 4. At such time, an enzymatic reaction caused by the immobilized enzyme 3 proceeds in the presence of a heterocyclic compound containing nitrogen and carbon atoms and having 5- or 6-membered ring in the bioreactor of the present invention. The heterocyclic compound containing nitrogen and carbon atoms and having 5- or 6-membered ring may be preliminarily mixed with the reaction solution. Alternatively, the compound and the reaction solution may be separately supplied to the chassis 4 so as to be mixed in the chassis 4. It is also possible to preliminarily provide the heterocyclic compound containing nitrogen and carbon atoms and having 5- or 6-membered ring to the chassis 4 by, for example, impregnating the support 1 with the compound.

In the bioreactor shown in FIG. 1, it is possible to discharge the reaction solution containing the substance of interest in the direction shown by arrow B after the end of the enzymatic reaction in the chassis 4. It is also possible to continuously produce the substance of interest by continuously supplying the reaction solution in the direction from arrow A to arrow B so as to continuously allow to the enzymatic reaction to proceed in the chassis 4 in the bioreactor shown in FIG. 1.

Figure 2:
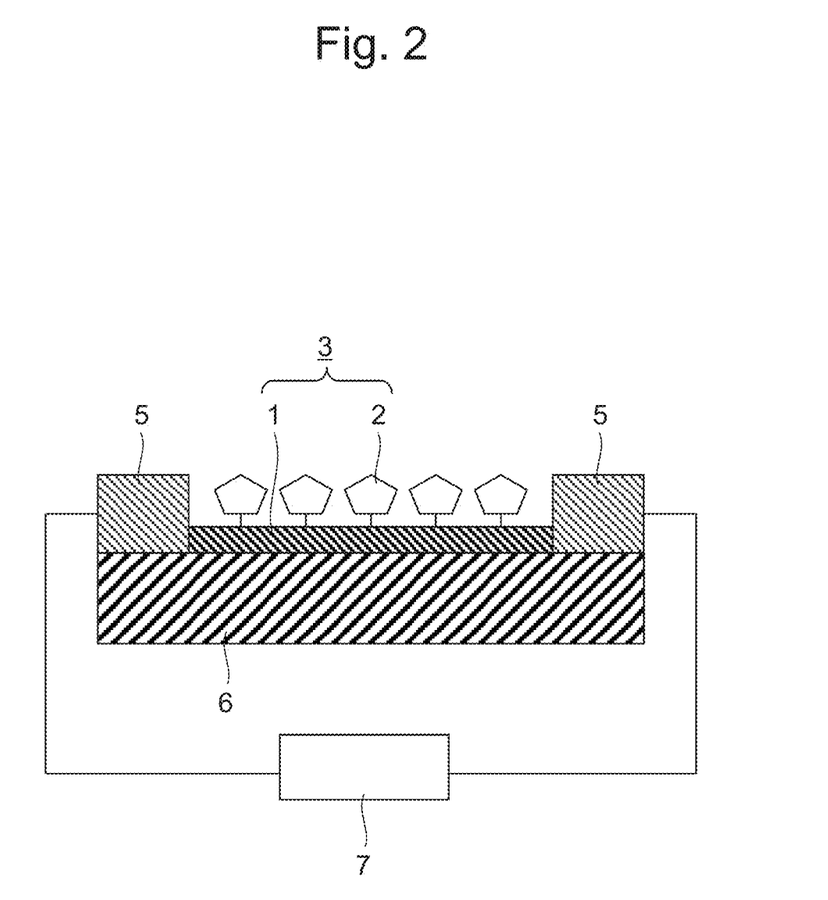
FIG. 2 schematically shows another example of the bioreactor of the present invention.

Further, FIG. 2 schematically shows another example of the bioreactor of the present invention. The bioreactor shown in FIG. 2 is configured to have an immobilized enzyme 3 obtained by immobilizing an enzyme 2 on a support 1, a pair of electrodes 5 that are disposed to sandwich the immobilized enzyme 3, a base plate 6 to which the immobilized enzyme 3 and the electrode 5 are attached, and a detector 7 that is electrically connected to the pair of electrodes 5. The bioreactor shown in FIG. 2 is intended to be used to electrically detect a change resulting from the progress of the enzymatic reaction caused by the immobilized enzyme 3. That is, the bioreactor shown in FIG. 2 is an apparatus (biosensor) for detecting a substance contained in a solution through an enzymatic reaction.

In the bioreactor shown in FIG. 2, a solution to be examined is allowed to come into contact with the immobilized enzyme 3. In order for the solution to come into contact with the immobilized enzyme 3, the solution may be added dropwise to the immobilized enzyme 3 or the bioreactor as a whole may be immersed in the solution. In a case in which the solution contains a substrate that reacts with the immobilized enzyme 3, the detector 7 can detect the current flowing between the pair of electrodes 5 generated by a redox reaction of a coenzyme (e.g., NADH) as a result of the progress of the enzymatic reaction. In this case, the enzymatic reaction caused by the immobilized enzyme 3 proceeds in the presence of a heterocyclic compound containing nitrogen and carbon atoms and having 5- or 6-membered ring in the bioreactor of the present invention. The heterocyclic compound containing nitrogen and carbon atoms and having 5- or 6-membered ring may be preliminarily mixed with the solution to be examined. Alternatively, the compound and the solution may be separately supplied to the immobilized enzyme 3 so as to be mixed with the immobilized enzyme 3. It is also possible to preliminarily impregnate the support 1 with the heterocyclic compound containing nitrogen and carbon atoms and having 5- or 6-membered ring.

The term "heterocyclic compound containing a 5- or 6-membered ring of nitrogen and carbon atoms" used herein refers to a compound obtained by substituting at least one carbon atom and preferably two carbon atoms with a nitrogen atom(s) in a compound containing a 5- or 6-membered ring of carbon atoms. The heterocyclic compound may be an aliphatic compound or an aromatic compound. Examples of an aliphatic heterocyclic compound containing a 5- or 6-membered ring of nitrogen atoms include, but are not particularly limited to, 2-imidazolidinone, piperidine, piperazine, morpholine, pyrrolidine, and derivatives thereof. Examples of an aromatic heterocyclic compound containing a 5- or 6-membered ring of nitrogen atoms include, but are not particularly limited to, pyrrole, imidazole, pyrazole, oxazole, isooxazole, thiazole, isothiazole, triazole, pyridine, pyrimidine, pyridazine, pyrazine, 1,2,3-triazine, bipyridine, and derivatives thereof. It is particularly preferable to use pyrazine, 2-imidazolidinone, and a compound containing an imidazole ring (an imidazole derivative or an imidazole compound). This is because the use of pyrazine, 2-imidazolidinone, and a compound containing an imidazole ring enables an immobilized enzyme to have significantly improved enzyme activity.

Examples of a compound containing an imidazole ring include, but are not particularly limited to, imidazole derivatives such as histidine, 1-vinylimidazole, 1-methylimidazole, 2-methylimidazole, 4-methylimidazole, 2-ethylimidazole, imidazole-2-carboxylate ethyl, imidazole-2-carboxaldehyde, imidazole-4-carboxylate, imidazole-4,5-dicarboxylate, imidazole-1-yl-acetic acid, 2-acetylbenzimidazole, 1-acetylimidazole, N-acetylimidazole, 2-aminobenzimidazole, N-(3-aminopropyl)imidazole, 5-amino-2-(trifluoromethyl)benzimidazole, 4-azabenzimidazole, 4-aza-2-mercaptobenzimidazole, benzimidazole, 1-benzylimidazole, and 1-butylimidazole, in addition to imidazole. Particularly preferably, imidazole, histidine, and/or 1-vinylimidazole are used as an imidazole compound. This is because the use of imidazole, histidine, and/or 1-vinylimidazole allows the significant improvement of enzyme activity of an immobilized enzyme.

As the compound containing an imidazole ring, polymers such as polyvinylimidazole, polybenzoimidazole, and derivatives thereof can be used. It is particularly preferable to use polyvinylimidazole. This is because the use of polyvinylimidazole allows the significant improvement of enzyme activity of an immobilized enzyme. In this regard, the molecular weights of the polymers are preferably 5000-1000000, more preferably 5000-200000, and most preferably 100000-200000.

In addition, the concentration of the imidazole compound in the reaction field is not particularly limited as long as the imidazole compound is mixed with a solution when used. However, it is preferably 0.2-5.0 M and more preferably 0.5-2.0 M. When the concentration of the imidazole compound falls within the above range, enzyme activity of the immobilized enzyme 3 can be further improved. If the concentration of the imidazole compound is below such range, the effects of improving the enzyme activity of the immobilized enzyme 3 might be reduced. In addition, if the concentration of the imidazole compound is above such range, reactivity might decrease due to an increase in viscosity of the solution, and the imidazole compound might become toxic to the immobilized enzyme 3.

Further, the concentration of the imidazole compound in the reaction field is preferably 2.0-50 nmol/cm$^2$ and more preferably 5.0-20 nmol/cm$^2$ when the imidazole compound is applied to a support and mixed thereon when used. When the concentration of the imidazole compound falls within the above range, enzyme activity of the immobilized enzyme 3 can be further improved. If the concentration of the imidazole compound is below such range, the enzyme activity of the immobilized enzyme 3 might be reduced. In addition, if the concentration of the imidazole compound is above such range, the imidazole compound might become toxic to the immobilized enzyme 3.

Meanwhile, the enzyme 2 used for the immobilized enzyme 3 in the bioreactor of the present invention is not particularly limited and thus it can be an arbitrary enzyme. That is, the present invention can be applied to a wide range of enzymes (immobilized enzymes) regardless of enzyme type.

Specific examples of the enzyme 2 include enzymes that catalyze reactions for producing desired products using given substrates in a case in which the enzyme 2 is used in the bioreactor shown in FIG. 1. Examples of such enzymes include, but are not particularly limited to, aminoacylase that converts acetyl-DL-amino acid to L-amino acid, glucose isomerase that converts glucose to an isomerized sugar, aspartase that converts fumaric acid to L-aspartic acid, penicillin amylase that converts penicillin G to 6-aminopenicillanic acid, fumarase that converts fumaric acid to L-malic acid, lactase that converts milk to low-lactose milk, L-aspartate-β-decarboxylase that converts L-asparagine to L-alanine, nitrile hydratase that converts acrylonitrile to acrylamide, alpha-glucosyltransferase that converts sucrose to palatinose, β-fructofuranosidase that converts sucrose to fructooligosaccharide, lipase that converts vegetable oil to cacao-butter-like fat and oil, maltooligosaccharide-producing enzyme that converts liquefied starch to maltooligosaccharide, glucose oxidase that converts albumen to dried albumen, naringinase that makes natural juice have no bitter taste, papain that prevents cloudiness in beer, lipase that converts vegetable oil to fatty acid, and acetate kinase that converts ADP to ATP.

In addition, specifically, when the enzyme 2 is used in the bioreactor shown in FIG. 2, an enzyme capable of functioning to specifically identify a certain molecule can be used. Specific examples of such enzyme include glucose oxidase for detecting glucose, cholesterol oxidase for detecting cholesterol, cholesterol esterase for detecting cholesterol ester, lipase for detecting triglyceride, alkaline phosphatase and phospholipase C for detecting phospholipid, acyl-CoA synthase for detecting free fatty acid, urease for detecting urea, glutamate dehydrogenase for detecting ammonia, uricase for detecting uric acid, creatininase for detecting creatinine, creatinase for detecting creatine, bilirubin oxidase for detecting bilirubin, methionine-γ-lyase for detecting methionine, lactate dehydrogenase for detecting lactic acid or pyruvic acid, L-amino acid oxidase for detecting amino acid, citrate lyase for detecting citric acid, and glycogen phosphorylase for detecting inorganic phosphoric acid.

The support 1 on which the enzyme 2 is immobilized is not particularly limited and thus a variety of supports (or carriers) which have been conventionally used for immobilized enzymes can be used. More specifically, examples of the support include polysaccharide derivatives having ion-exchange groups, synthetic polymers such as ion-exchange resins, porous alkylamine glass, nylon polystyrene, polyacrylamide, polyvinyl alcohol, starch, collagen, and polyurethane. In addition, conventionally known methods can be adequately used as a method for immobilizing the enzyme 2 on the support 1. Specifically, enzyme immobilization methods are roughly classified into carrier-binding methods, cross-linking methods, and inclusion methods. Carrier-binding methods include adsorption methods, covalent bonding methods, and ion bonding methods. Cross-linking methods are intended to bind the support 1 and the enzyme 2 with the use of a variety of cross-linkers. Inclusion methods are intended to encapsulate enzymes into polymers.

In the bioreactor of the present invention with the above configuration, an enzymatic reaction caused by the immobilized enzyme 3 proceeds in the presence of an imidazole compound. Therefore, enzyme activity of the immobilized enzyme 3 is significantly improved. For example, in the bioreactor shown in FIG. 1, productivity of a substance is significantly improved. Also, in the bioreactor shown in FIG. 2, a substance can be detected with high sensitivity. In addition, the bioreactor of the present invention is not limited to the configurations of the bioreactors shown in FIGS. 1 and 2. Thus, it can be applied to so-called enzyme columns, enzyme tubes, enzyme membranes, autoanalyzers, and flow injection analyzers (FIAs).

<Biofuel Cell>

The biofuel cell of the present invention is a biofuel cell comprising a cathode electrode and an anode electrode that face each other across an electrolyte, wherein the cathode electrode, the anode electrode, or both thereof have an immobilized enzyme. In the biofuel cell, an enzymatic reaction caused by an immobilized enzyme included in an electrode proceeds in the presence of the heterocyclic compound containing nitrogen and carbon atoms and having 5- or 6-membered ring described above. In addition, the biofuel cell of the present invention is not limited in terms of shape, enzyme type, electrolyte type, and the like as long as it is a battery cell using an enzymatic reaction caused by an immobilized enzyme.

Figure 3:
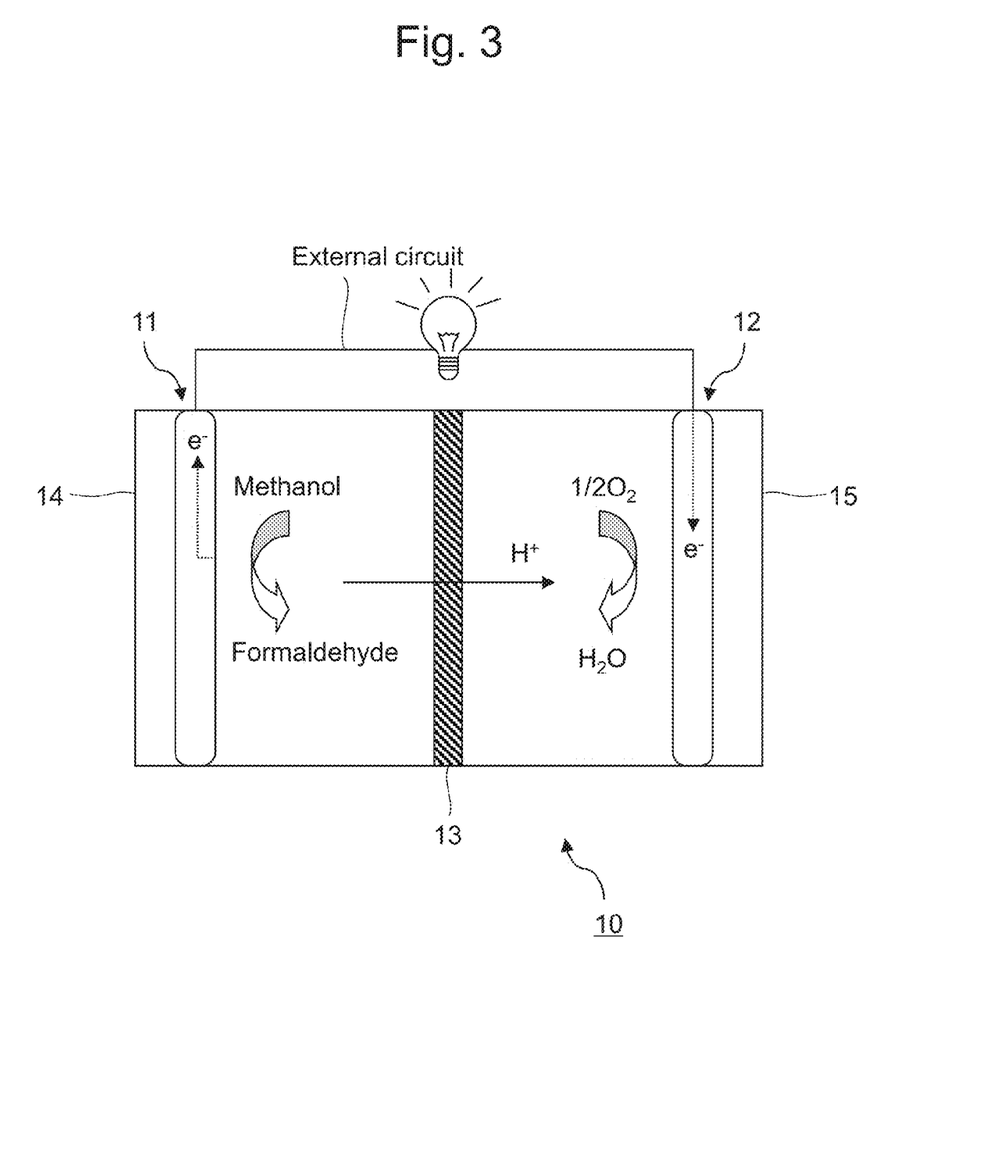
FIG. 3 schematically shows an example of the biofuel cell of the present invention.

FIG. 3 schematically shows an example of the biofuel cell of the present invention. A biofuel cell 10 shown in FIG. 3 comprises an anode electrode 11, a cathode electrode 12, and a membrane 13 (hereafter referred to as "electrolyte membrane 13") having ion conductivity which is disposed between the anode electrode 11 and the cathode electrode 12. In the biofuel cell 10, the anode electrode 11 is disposed in an anode chamber 14, and the cathode electrode 12 is disposed in a cathode chamber 15. The anode chamber 14 is charged or supplied with a fuel.

Particularly preferably, an immobilized enzyme is used for the anode electrode 11 such that an enzymatic reaction caused by the immobilized enzyme proceeds in the presence of the heterocyclic compound containing nitrogen and carbon atoms and having 5- or 6-membered ring described above in the biofuel cell of the present invention. Alternatively, an immobilized enzyme may be used for both of the anode electrode 11 and the cathode electrode 12 such that an enzymatic reaction caused by the immobilized enzyme proceed in the presence of the heterocyclic compound containing nitrogen and carbon atoms and having 5- or 6-membered ring described above in the biofuel cell of the present invention. Note that the type and the concentration of a heterocyclic compound containing nitrogen and carbon atoms and having 5- or 6-membered ring that can be used in the biofuel cell of the present invention are the same as those specified in the above descriptions of the bioreactor.

The heterocyclic compound containing nitrogen and carbon atoms and having 5- or 6-membered ring may be preliminarily mixed with a fuel charged or supplied to the anode chamber 14 or it may be supplied to the anode chamber 14 separately from the fuel in the biofuel cell of the present invention. Similarly, the heterocyclic compound containing nitrogen and carbon atoms and having 5- or 6-membered ring may be preliminarily mixed with a solution charged or supplied to the cathode chamber 15 or it may be supplied to the cathode chamber 15 separately from the solution in the biofuel cell of the present invention. Also, the heterocyclic compound containing nitrogen and carbon atoms and having 5- or 6-membered ring may be present on the surface of the anode electrode 11, with which a fuel comes into contact, and/or the surface of the cathode electrode 12, with which a solution comes into contact, in the biofuel cell of the present invention. For example, a solution containing the heterocyclic compound containing nitrogen and carbon atoms and having 5- or 6-membered ring is applied to the surface of the anode electrode 11, with which a fuel comes into contact and/or the surface of the cathode electrode 12, with which a solution comes into contact, thereby allowing the heterocyclic compound to be present on the surface. Alternatively, when an electrode material that constitutes the anode electrode 11 or the cathode electrode 12 is prepared, the heterocyclic compound containing nitrogen and carbon atoms and having 5- or 6-membered ring may be preliminarily mixed with the electrode material.

Here, the anode electrode 11 comprises an electrode material and an agent for oxidation reactions containing an enzyme and a mediator. The mediator contained in the agent for oxidation reactions of the anode electrode 11 is a bio-derived protein capable of transferring electrons, which transfer electrons between the enzyme contained in the agent for oxidation reactions and the electrode material. Examples of such bio-derived protein capable of transferring electrons include, but are not particularly limited to, metal-containing proteins containing iron, copper, and the like, such as hemoglobin, ferredoxin, cytochrome C511, cytochrome P450, azurin, plastocyanin, cytochromes a, a1, a3, b, b2, b3, b5, b6, b555, b559, b562, b563, b565, b566, c, c1, c2, c3, d, e, f, o, and P-450, hemocyanin, and ferritin.

More specifically, examples of the bio-derived protein capable of transferring electrons include bovine-derived hemoglobin (manufactured by NACALAI TESQUE, INC.), *Clostridium*-derived ferredoxin (manufactured by SIGMA), *Pseudomonas*-derived cytochrome C551 (manufactured by SIGMA), and *Pseudomonas*-derived azurin (manufactured by SIGMA).

The enzyme contained in the agent for oxidation reactions of the anode electrode 11 is involved in an oxidation reaction of a fuel charged or supplied to the anode chamber 14. It is selected depending on fuels exemplified below. For example, when methanol is used as a fuel, an example of the enzyme is alcohol dehydrogenase that oxidizes methanol to formaldehyde. In addition, for example, when glucose is used as a fuel, an example thereof is glucose dehydrogenase that oxidizes glucose to gluconolactone. These enzymes are preferably $NAD^+$-dependent dehydrogenases or PQQ (pyrroloquinoline quinone) dehydrogenases. In the cases of $NAD^+$-dependent dehydrogenases, NAD (nicotinamide adenine dinucleotide) is used as a coenzyme such that an oxidation reaction of a fuel proceeds in the presence of $NAD^+$. Meanwhile, in the cases of PQQ (pyrroloquinoline quinone) dehydrogenases, an oxidation reaction of a fuel proceeds even in the absence of NAD that functions as a coenzyme.

Specific examples of PQQ dehydrogenases that can be used include: PQQ alcohol dehydrogenases from *Acetobacter pasteurianus, Methylobacterium extorquens, Paracoccus denitrificans, Pseudomonas putida*, and *Comamonas testosteroni* (NBRC 12048); and PQQ glucose dehydrogenases from *Acetobacter calcoaceticus* and *Escherichia coli*.

In addition to the above, examples of the enzyme contained in the agent for oxidation reactions that can be used include enzymes involved in sugar metabolism (e.g., hexokinase, glucose phosphate isomerase, phosphofructokinase, fructose-bisphosphate aldolase, triosephosphate isomerase, glyceraldehyde phosphate dehydrogenase, phosphoglyceromutase, phosphopyruvate hydratase, pyruvate kinase, L-lactate dehydrogenase, D-lactate dehydrogenase, pyruvate dehydrogenase, citrate synthase, aconitase, isocitrate dehydrogenase, 2-oxoglutarate dehydrogenase, succinyl-CoA synthetase, succinate dehydrogenase, fumarase, and malonate dehydrogenase).

Examples of the fuel to be charged or supplied to the anode chamber 14 that can be used include alcohols such as methanol, sugars such as glucose, fats, proteins, organic acids obtained as intermediate products of sugar metabolism (glucose-6-phosphate, fructose-6-phosphate, fructose-1,6-bisphosphate, triosephosphate isomerase, 1,3-bisphosphoglycerate, 3-phosphoglycerate, 2-phosphoglycerate, phosphoenolpyruvate, pyruvic acid, acetyl-CoA, citric acid, cis-aconitic acid, isocitric acid, oxalosuccinic acid, 2-oxoglutaric acid, succinyl-CoA, succinic acid, fumaric acid, L-malic acid, and oxaloacetic acid), and mixtures thereof.

It is preferable to use, as the electrode material, a porous material because the amount of an agent for oxidation reactions containing an enzyme and a mediator to be absorbed or immobilized on the electrode material can be increased. Examples of a porous material include carbon felt, carbon paper, and activated carbon The anode electrode 11 is not particularly limited. For example, an immobilized enzyme can be prepared by immobilizing an agent for oxidation reactions containing an enzyme and a mediator on an electrode material using a polymer or a cross-linker. Alternatively, an immobilized enzyme for the anode electrode 11 can be prepared by, for example, dissolving an agent for oxidation reactions containing an enzyme and a mediator in a buffer solution and immersing an electrode material in the solution in which the agent has been dissolved. Examples of a polymer that can be used herein include polyvinyl imidazole, polyallylamine, polyamino acid, polypyrrole, polyacrylic acid, polyvinylalcohol, a graft copolymer of polypropylene and maleic anhydride, a copolymer of methylvinyl ether and maleic anhydride, and an ortho-cresol novolac epoxy resin. In addition, examples of a cross-linker that can be used include polyethylene glycol diglycidyl ether, glutaraldehyde, disuccinimidyl suberate, and succinimidyl-4-(p-phenylmaleimide) butyrate. Further, a buffer solution that can be used include an MOPS(3-(N-morpholino)propanesulfonic acid) buffer solution, a phosphate buffer solution, and a Tris buffer solution.

Next, the cathode electrode 12 is described. The cathode electrode 12 is composed of an electrode material and an agent for reduction reactions. An agent for reduction reactions that can be used for the cathode electrode 12 comprises, for example, a carbon powder carrying, as an electrode catalyst, a metal catalyst such as platinum, or it comprises a mediator and an oxygen-reducing enzyme.

Examples of an oxygen-reducing enzyme that can be used as an agent for reduction reactions include bilirubin oxidase, laccase, and peroxidase. In addition, examples of a mediator that can be used include those similar to the aforementioned examples. Meanwhile, if an agent for reduction reactions comprises a carbon powder carrying a metal catalyst, examples of a metal catalyst that can be used include platinum, iron, nickel, cobalt, and ruthenium. In addition, examples of a carbon powder that can be used include carbon black such as acetylene black, furnace black, channel black, thermal black, and so on.

In the cathode electrode 12 inside the cathode chamber 15, a reaction that generates water from oxygen ions and protons proceeds. Therefore, the cathode electrode 12 needs to be supplied with oxygen to be used in the reaction. For example, it is possible to supply oxygen to be used in the reaction by introducing a gas containing oxygen (e.g., air) to the cathode chamber 15. Alternatively, it is also possible to supply a buffer solution (containing oxygen) supplemented with a sacrificial reagent such as potassium ferricyanide to the cathode chamber 15. In addition, oxygen gas may be used if an agent used for reduction reactions that constitutes the cathode electrode 12 is a carbon powder carrying a metal catalyst such as platinum.

When an oxygen-reducing enzyme and a mediator are used as an agent for reduction reactions, an immobilized enzyme can be prepared as the cathode electrode 12 by immobilizing an oxygen-reducing enzyme and a mediator on an electrode material with the use of a polymer and a cross-linker, as in the case of the anode electrode 11 described above. Alternatively, for example, it is also possible to prepare an immobilized enzyme that can be used for the cathode electrode 12 by dissolving an oxygen-reducing enzyme and a mediator in a buffer solution and immersing an electrode material in the solution. A polymer, a cross-linker, and a buffer solution that can be used herein are similar to those used for the anode electrode 11 described above. Meanwhile, if a carbon powder carrying a metal catalyst is used, a carbon powder carrying a metal catalyst is immobilized on an electrode material with the use of an electrolyte (e.g., a perfluorocarbon sulfonate-based electrolyte) that is similar to that used for an electrolyte membrane 13 described below for the cathode electrode 12.

In addition, an electrolyte membrane 13 is not particularly limited as long as it has proton conductivity but not electron conductivity. Examples of the electrolyte membrane 13 include a perfluorocarbon sulfonate-based resin membrane, a copolymer membrane of a trifluorostyrene derivative, a polybenzimidazole membrane impregnated with phosphoric acid, and an aromatic polyether ketone sulfonate membrane. One specific example is Nafion (registered trademark). In addition, it is also possible to allow the electrolyte membrane 13 to contain the heterocyclic compound containing nitrogen and carbon atoms and having 5- or 6-membered ring described above in the biofuel cell of the present invention. Meanwhile, the electrolyte membrane 13 does not necessarily contain the heterocyclic compound containing nitrogen and carbon atoms and having 5- or 6-membered ring.

In the biofuel cell 1 of the present invention that is composed in the above manner, when, for example, methanol is used as a fuel to be supplied to the anode electrode 11, a redox reaction in the anode electrode 11 and that in the cathode electrode 12 are expressed by the following formula (1) and (2), respectively.

$$\text{Anode: } CH_3OH \rightarrow HCHO + 2H^+ + 2e^- \quad (1)$$

$$\text{Cathode: } 2H^+ + \tfrac{1}{2}O_2 + 2e^- \rightarrow H_2O \quad (2)$$

That is, a reaction in which an enzyme converts methanol to formaldehyde, hydrogen ions, and electrons takes place in the anode electrode 11. The electrons are transferred by the mediator to the electrode material and further transferred via an external circuit to the cathode electrode 12. The hydrogen ions migrate to the cathode electrode 12 through the electrolyte membrane 13. Meanwhile, a reaction that causes hydrogen ions, electrons, and oxygen ions to react with each other so as to produce water takes place in the cathode electrode 12. As a result of these reactions, energy is released into the external circuit.

In particular, the biofuel cell of the present invention has improved fuel cell characteristics, such as fuel cell power output, compared with conventional biofuel cells. Here, conventional biofuel cells are fuel cells in which an enzymatic reaction caused by an immobilized enzyme that constitutes an electrode proceeds in the absence of a heterocyclic compound containing nitrogen and carbon atoms and having 5- or 6-membered ring. In this regard, the biofuel cell of the present invention is characterized in that an enzymatic reaction caused by an immobilized enzyme that constitutes an anode electrode proceeds in the presence of the heterocyclic compound containing nitrogen and carbon atoms and having 5- or 6-membered ring described above. Therefore, enzyme activity of the immobilized enzyme that constitutes an anode electrode can be significantly improved.

EXAMPLES

The present invention is described in more detail with reference to the Examples below; however, the technical scope of the present invention is not limited to the Examples.

Examples 1-3

In Examples 1 to 3, imidazole compounds were used as a heterocyclic compound containing nitrogen and carbon atoms and having 5- or 6-membered ring to evaluate enzyme activity of a variety of immobilized enzymes in the presence of the imidazole compounds.

(1-1) Preparation of Immobilized Enzymes

A support was applied a fibrous base material cut in pieces 1 cm$^2$ in area, followed by drying. Each piece of fibrous base material was allowed to absorb a liquid obtained by mixing 2.5% glutaraldehyde, 20% poly-L-lysine, 10 mM Tris-HCl (pH 8.0), and a different one of the enzymes of Examples 1-3, followed by drying. Thus, immobilized enzymes were prepared. Table 1 lists enzymes used in Examples 1-3.

TABLE 1

|  | Enzyme | Substrate |
| --- | --- | --- |
| Example 1, Comparative Example 1 | Glucose dehydrogenase | Glucose, NADP |
| Example 2, Comparative Example 2 | Glutamate dehydrogenase | Monosodium glutamate, NADP |
| Example 3, Comparative Example 3 | Formate dehydrogenase | Sodium formate, NAD |

Glucose dehydrogenase, glutamate dehydrogenase, and formate dehydrogenase used in the Examples were those manufactured by TOYOBO CO., LTD., Funakoshi Corporation, and Sigma-Aldrich Co. LLC., respectively.

(1-2) Evaluation of Immobilized Enzymes Using Imidazole

In each of Examples 1-3, the immobilized enzyme was immersed in a solution prepared by mixing the corresponding substrate listed in table 1 and 1M imidazole HCl (pH 7.0). The solution was stirred at 25° C. for 30 minutes to allow the enzyme to react with the substrate. Then, WST1 and mPMS were added for color development. Absorbance was measured with a spectrophotometer. Meanwhile, in Comparative Examples 1-3, the immobilized enzymes were evaluated as in the cases of Examples 1-3, except that 1M sodium phosphate buffer (pH 7.0) was used instead of 1M imidazole HCl (pH 7.0).

Glucose, sodium glutamate, NAD, and NADP used in the Examples were those manufactured by NACALAI TESQUE, INC.

(1-3) Results

Figure 4:
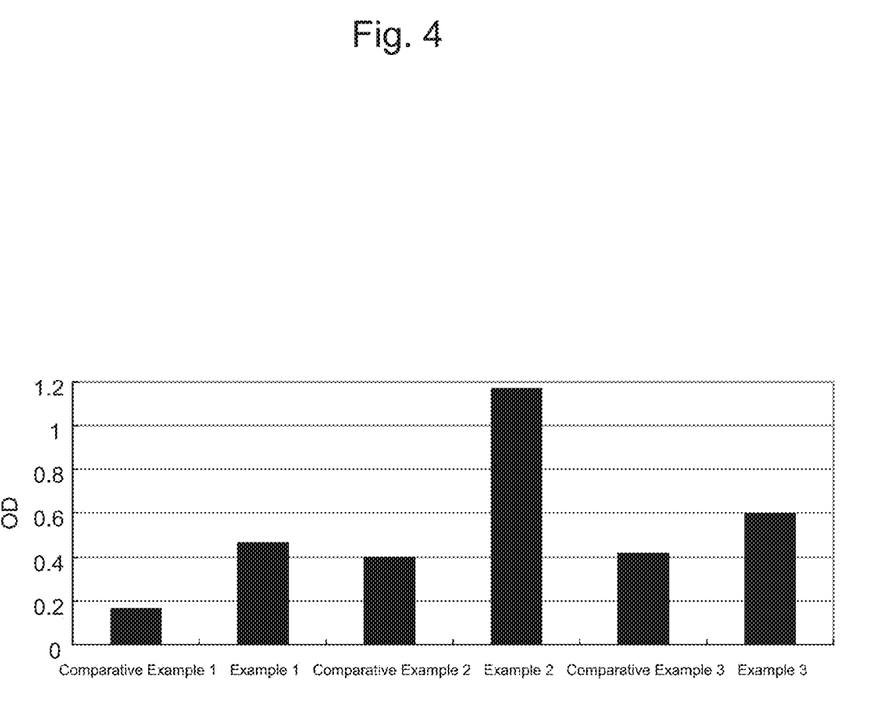
FIG. 4 is a characteristic diagram showing the results of determination of enzyme activity for different immobilized enzymes in the presence or absence of an imidazole compound.

Table 2 and FIG. 4 show the results obtained in Examples 1-3 and Comparative Examples 1-3.

TABLE 2

|  | OD |
| --- | --- |
| Example 1 | 0.4668 |
| Example 2 | 1.1707 |
| Example 3 | 0.5996 |
| Comparative Example 1 | 0.1598 |
| Comparative Example 2 | 0.3966 |
| Comparative Example 3 | 0.4134 |

As is understood from table 2 and FIG. 4, the immobilized enzymes were found to have excellent enzyme activity in the presence of the imidazole compounds. The above results revealed that enzyme activity can be significantly improved for a bioreactor comprising an immobilized enzyme by allowing the immobilized enzyme to cause an enzymatic reaction in the presence of an imidazole compound.

In particular, in Examples 1-3, it was shown that it is possible to significantly improve enzyme activity of an immobilized enzyme which is obtained by immobilizing an oxidoreductase so that it can be used for an anode electrode of a biofuel cell. The above results indicate that excellent fuel cell characteristics can be imparted to a biofuel cell comprising an immobilized enzyme that is obtained using an oxidoreductase with the significant improvement of enzyme activity, especially in an anode electrode.

Examples 4-8

In Examples 4-8, a variety of heterocyclic compounds each containing a 5- or 6-membered ring of nitrogen and carbon atoms were used in order to evaluate their effects of improving the enzyme activity of immobilized enzymes.

(1-1) Preparation of Immobilized Enzymes

A support was applied a fibrous base material cut in pieces 1 cm$^2$ in area, followed by drying. Each piece of fibrous base material was allowed to absorb a liquid obtained by mixing 2.5% glutaraldehyde, 20% poly-L-lysine, 10 mM Tris-HCl (pH 8.0), and formate dehydrogenase, followed by drying. Thus, immobilized enzymes were prepared.

(1-2) Evaluation of the Effects of Heterocyclic Compounds Upon the Improvement of Activity of Immobilized Enzymes In Examples 4-8, the compounds listed in table 3 were used as heterocyclic compounds. The molecular weight of polyvinyl imidazole used in Example 7 was 111500.

TABLE 3

|  | Heterocyclic compound |
| --- | --- |
| Example 4 | 1M Pyrazine |
| Example 5 | 1M 2-Imidazolidinone |
| Example 6 | 1M 1-Vinylimidazole |
| Example 7 | 1M Polyvinylimidazole |
| Example 8 | 0.2M Histidine |

The immobilized enzyme was immersed in a solution mixed with the corresponding heterocyclic compound listed in table 3. The solution was stirred at 25° C. for 30 minutes to induce a reaction. Then, WST1 and mPMS were added for color development. Absorbance was measured with a spectrophotometer (Infinite M200 manufactured by TECAN). Meanwhile, in Comparative Example 2, the immobilized enzyme was evaluated in the same manner, except that 1M sodium phosphate buffer (pH 7.0) was used instead of the heterocyclic compound.

(1-3) Results

Figure 5:
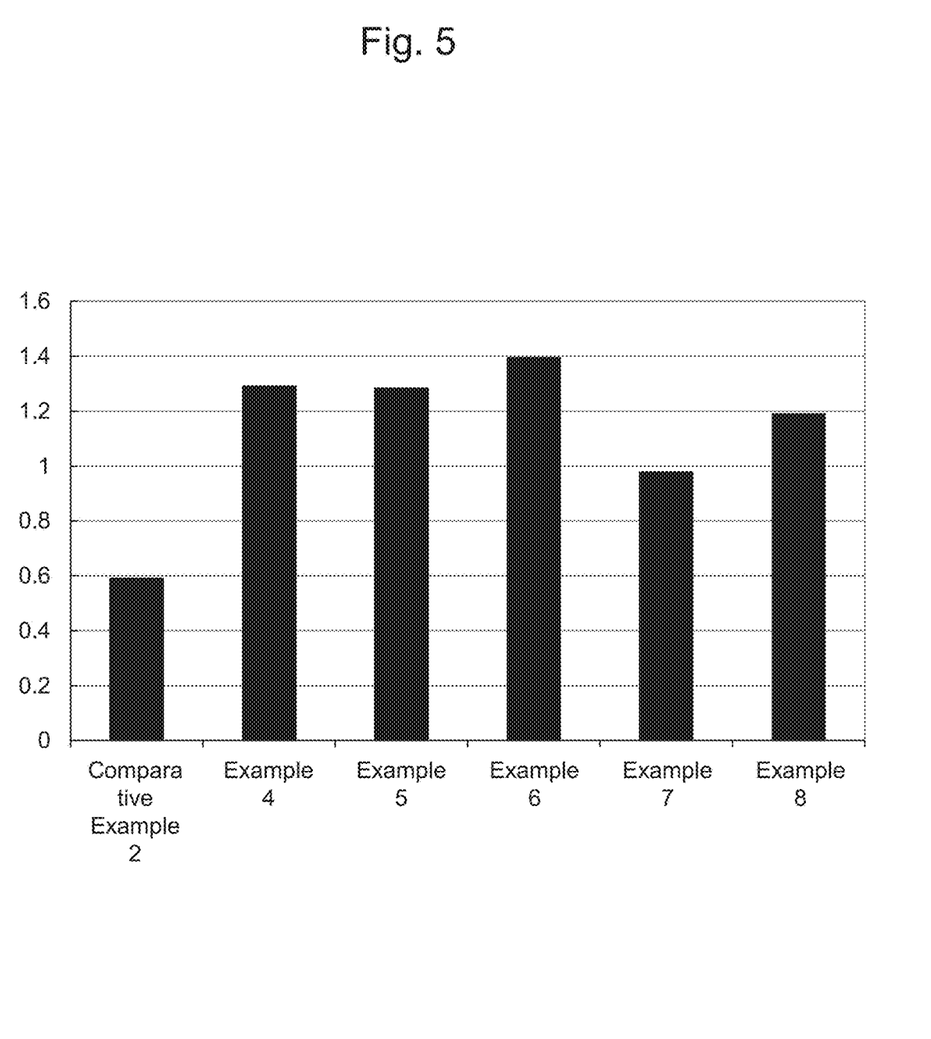
FIG. 5 is a characteristic diagram showing the results of determination of enzyme activity for an immobilized enzyme in the presence or absence of different heterocyclic compounds.

Table 4 and FIG. 5 show the results obtained in Examples 4-8 and Comparative Example 2.

TABLE 4

|  | OD |
| --- | --- |
| Example 4 | 1.2912 |
| Example 5 | 1.2841 |
| Example 6 | 0.9795 |
| Example 7 | 1.3948 |
| Example 8 | 1.1902 |
| Comparative Example 2 | 0.5909 |

As is understood from table 4 and FIG. 5, the immobilized enzymes were found to have excellent enzyme activity in the presence of a heterocyclic compound containing nitrogen and carbon atoms and having 5- or 6-membered ring such as pyrazine, 2-imidazolidinone, 1-vinylimidazole, polyvinyl imidazole, or histidine. The above results revealed that enzyme activity can be significantly improved for a bioreactor comprising an immobilized enzyme by allowing the immobilized enzyme to cause an enzymatic reaction in the presence of a heterocyclic compound containing nitrogen and carbon atoms and having 5- or 6-membered ring.

In particular, the use of pyrazine, 2-imidazolidinone, or 1-vinylimidazole as a heterocyclic compound containing nitrogen and carbon atoms and having 5- or 6-membered ring allows the immobilized enzyme to have significantly improved enzyme activity.

Also in Examples 4-8, it was shown that it is possible to significantly improve enzyme activity of an immobilized enzyme (immobilized formate dehydrogenase) which is obtained by immobilizing an oxidoreductase so that it can be used for an anode electrode of a biofuel cell. The above results indicate that excellent fuel cell characteristics can be imparted to a biofuel cell comprising an immobilized enzyme that is obtained using an oxidoreductase with the significant improvement of enzyme activity, especially in an anode electrode.

All publications, patents, and patent applications cited herein are incorporated herein by reference in their entirety.

The invention claimed is:

1. A biofuel cell, comprising:
a cathode electrode, an anode electrode, and an electrolyte, wherein
the cathode electrode and the anode electrode face each other across the electrolyte,
the anode electrode comprises an immobilized enzyme,
a surface of the anode electrode with which a fuel comes into contact comprises a heterocyclic compound,
the immobilized enzyme is allowed to cause an enzymatic reaction in the presence of the heterocyclic compound,
the electrolyte does not contain the heterocyclic compound, and
the heterocyclic compound is selected from the group consisting of pyrazine, 2-imidazolidinone and 1-vinylimidazole.

2. The biofuel cell according to claim 1, wherein the heterocyclic compound is contained in a fuel that comes into contact with the anode electrode.

3. The biofuel cell according to claim 1, wherein a concentration of the heterocyclic compound is adjusted to 0.2-5.0 M in order to realize the enzymatic reaction.

4. The biofuel cell according to claim 1, wherein the immobilized enzyme is obtained by immobilizing an oxidoreductase on a support.

5. The biofuel cell according to claim 4, wherein the oxidoreductase is an enzyme that catalyzes a redox reaction with the use of NAD and/or NADP as an electron acceptor.

6. The biofuel cell according to claim 4, wherein the oxidoreductase is one enzyme selected from the group consisting of glucose-1-dehydrogenase, glutamate dehydrogenase, and formate dehydrogenase.

7. The biofuel cell according to claim 1, wherein the cathode electrode comprises an immobilized enzyme, and the immobilized enzyme of the cathode electrode is allowed to cause an enzymatic reaction in the presence of a heterocyclic compound containing nitrogen and carbon atoms and having 5- or 6-membered ring.

8. The biofuel cell according to claim 7, wherein the heterocyclic compound is present on a surface of the cathode electrode with which a fuel comes into contact.

* * * * *